United States Patent [19]

Hagan et al.

[11] Patent Number: 5,046,645

[45] Date of Patent: Sep. 10, 1991

[54] SYPHON PACKAGE WITH MECHANICALLY ATTACHED VALVE

[75] Inventors: Richard J. Hagan, Millbrae; Michael D. Clausen, Turlock, both of Calif.

[73] Assignee: McKesson Corporation, San Francisco, Calif.

[21] Appl. No.: 566,348

[22] PCT Filed: Feb. 17, 1989

[86] PCT No.: PCT/US89/00599

§ 371 Date: Sep. 28, 1990

§ 102(e) Date: Sep. 28, 1990

[87] PCT Pub. No.: WO89/07559

PCT Pub. Date: Aug. 24, 1989

Related U.S. Application Data

[63] Continuation-in-part of Ser. No. 158,229, Feb. 19, 1988, abandoned.

[51] Int. Cl.$^5$ .............................................. B65D 83/00
[52] U.S. Cl. ............................... 222/394; 137/516.29; 222/518; 222/545; 251/149.6
[58] Field of Search ............... 222/324, 399, 212, 511, 222/518, 545, 546; 215/3-5, 232, 260; 285/162; 251/149.6, 149.7; 137/516.29, 903

[56] References Cited

U.S. PATENT DOCUMENTS

| | | | |
|---|---|---|---|
| 3,568,977 | 3/1971 | Nelson | 285/162 X |
| 3,863,673 | 2/1975 | Sitton | 222/545 X |
| 4,445,530 | 5/1984 | Credle | 251/149.6 X |
| 4,597,511 | 7/1986 | Licari | 137/903 X |
| 4,773,571 | 9/1988 | Hagan et al. | 222/394 |

Primary Examiner—Donald T. Hajec
Attorney, Agent, or Firm—Flehr, Hohbach, Test, Albritton & Herbert

[57] ABSTRACT

A syphon seltzer package (10) consists of a polyethylene terephthalate (PET) plastic bottle (12) with a neck (16) having an opening (18), into which a valve insert (20) is mounted. The insert (20) is held in place by mechanical attachment. The insert (20) fits into a sleeve (50) in an interference fit. Projections (52) on the outside of wall (32) insure a positive seal between the insert (20) and the sleeve (50). Similar projections (54) on the outside surface (56) of the sleeve (50) provide a positive seal between the sleeve (50) and the neck (16) of the bottle (12). At the bottom of the sleeve (50), there are four projections (58) spaced at 90 degree intervals around the sleeve (50). Castellations (60) are provided around the sleeve (50) between the projections (58). To assemble the package (20), the sleeve is inserted in the neck (16). The insert (20) is then driven into the sleeve (50). An interference fit between the insert (20) and the sleeve (50) causes the projections (58) and the castellations (60) to splay outward when the insert (20) is fully driven into the sleeve (50). The outward splaying of the projections (58) and castellations (60) locks the sleeve (50) and insert (20) in place in the neck (16) of the bottle (12).

23 Claims, 8 Drawing Sheets

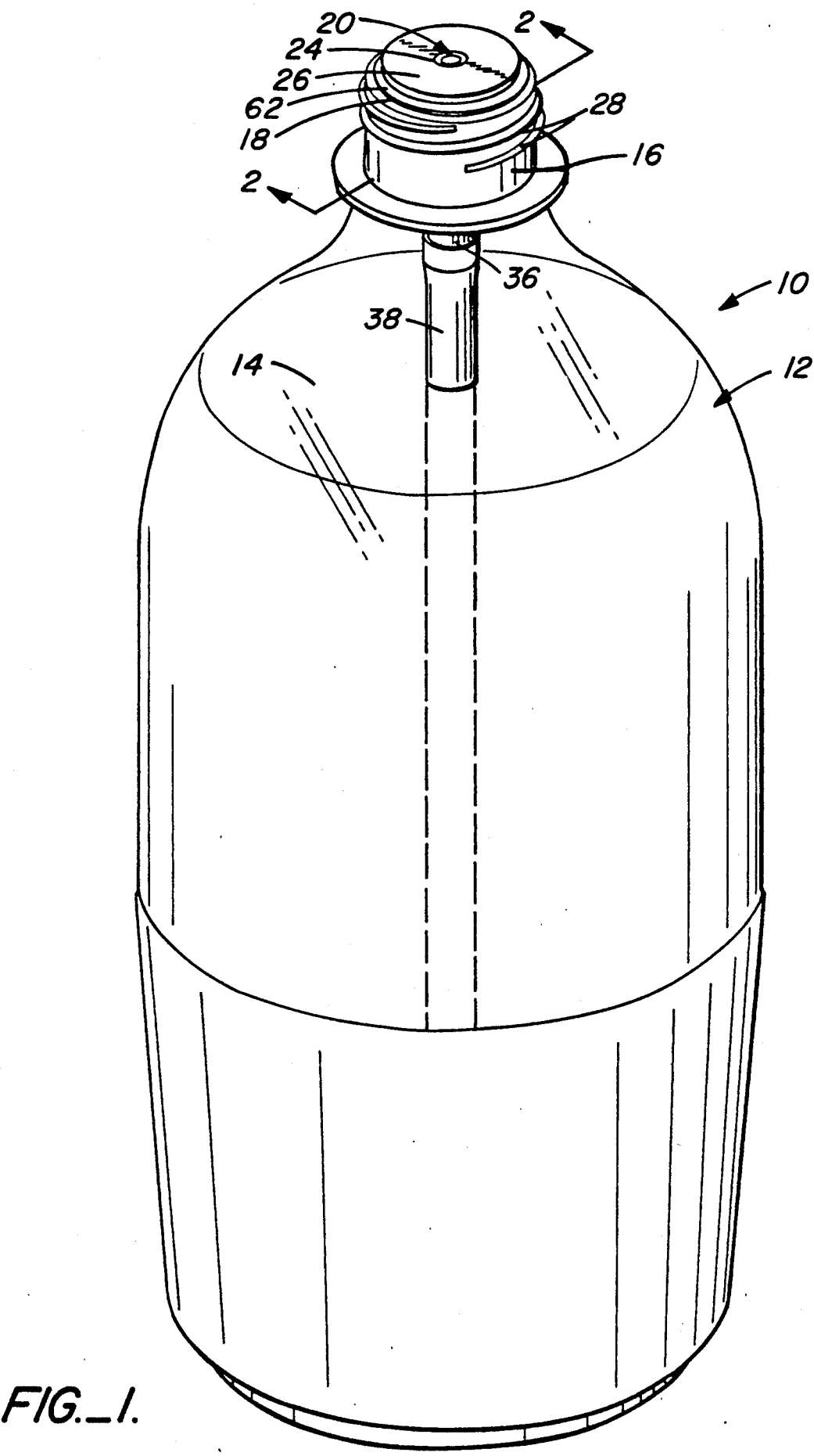
FIG._1.

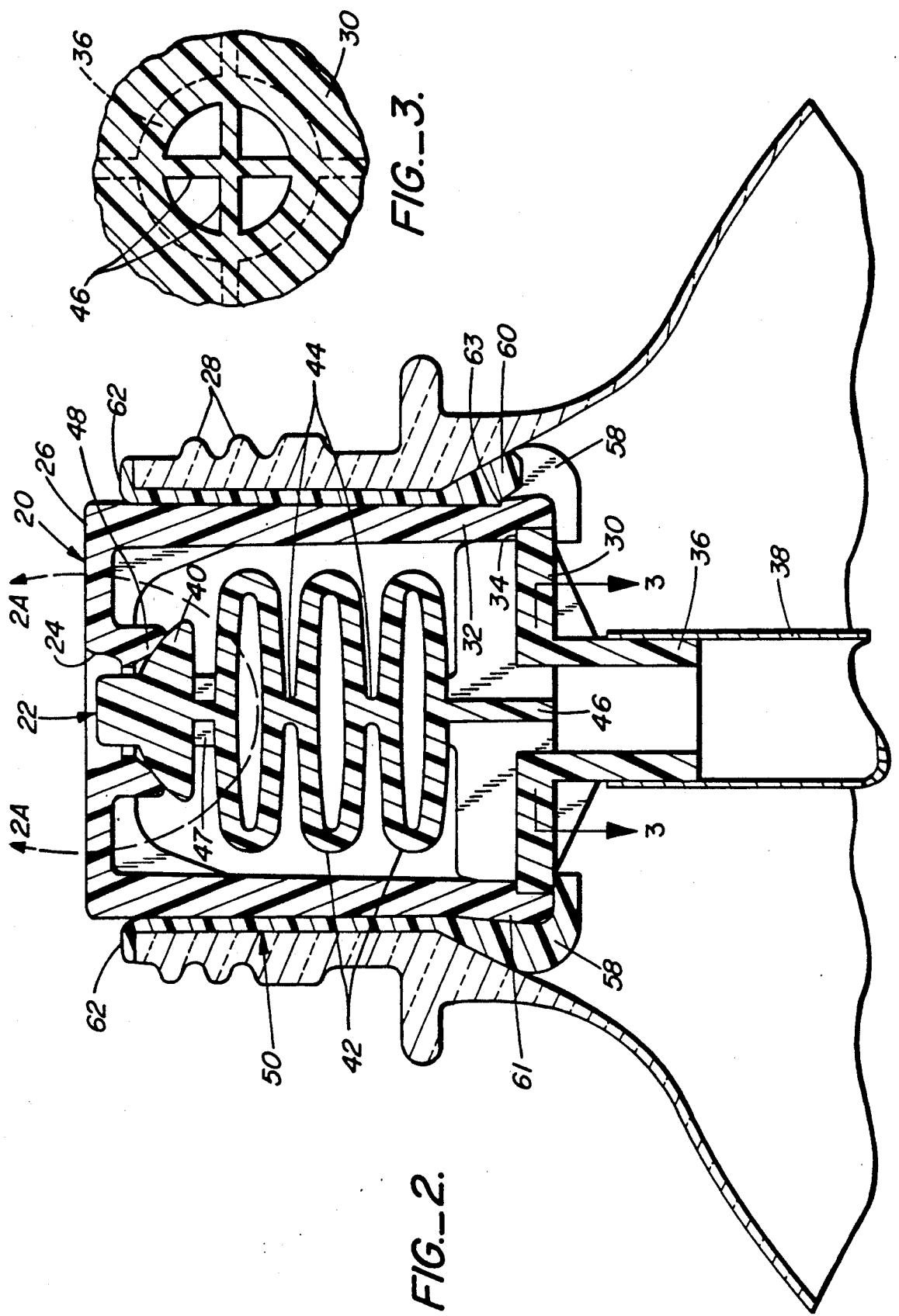

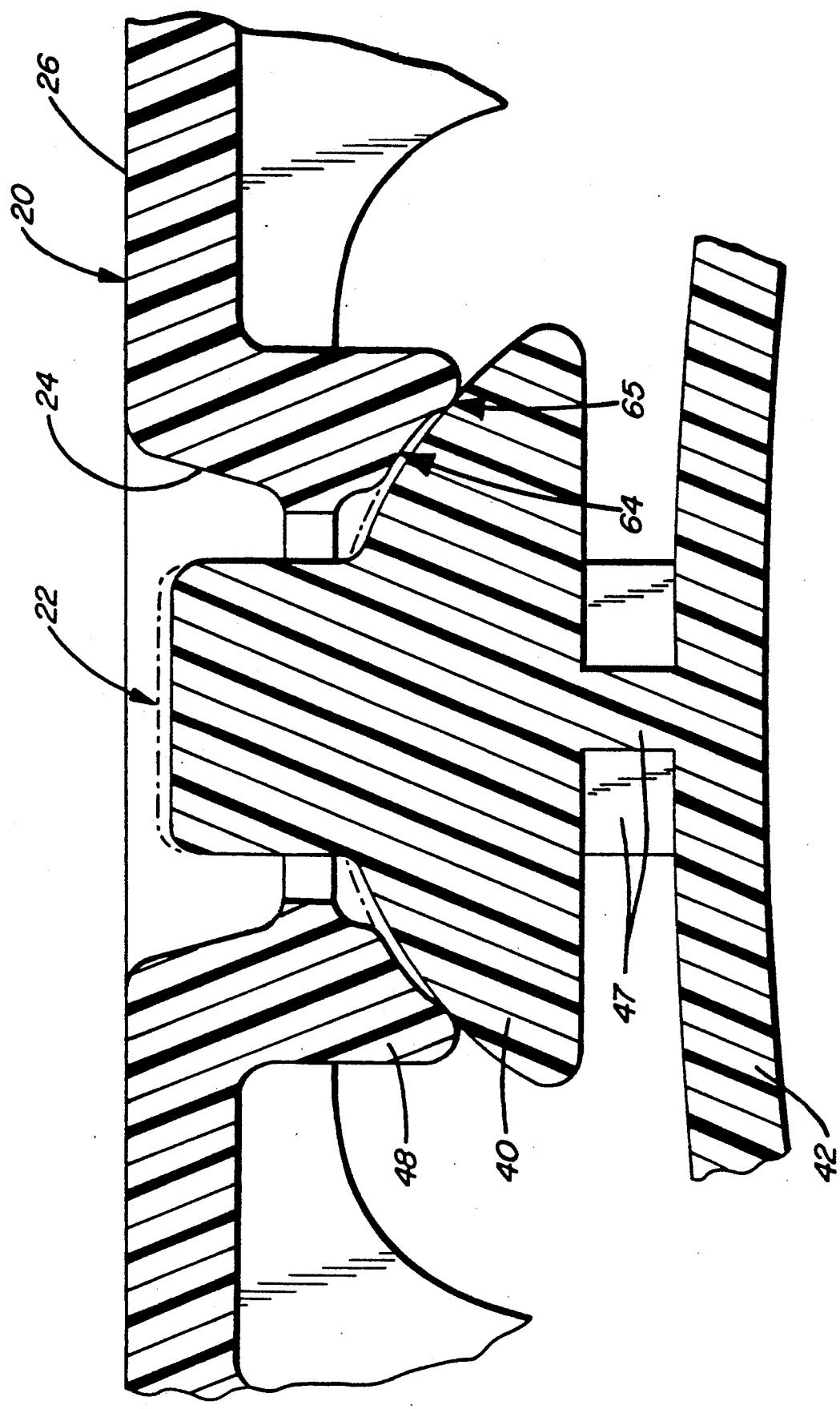
FIG._2A.

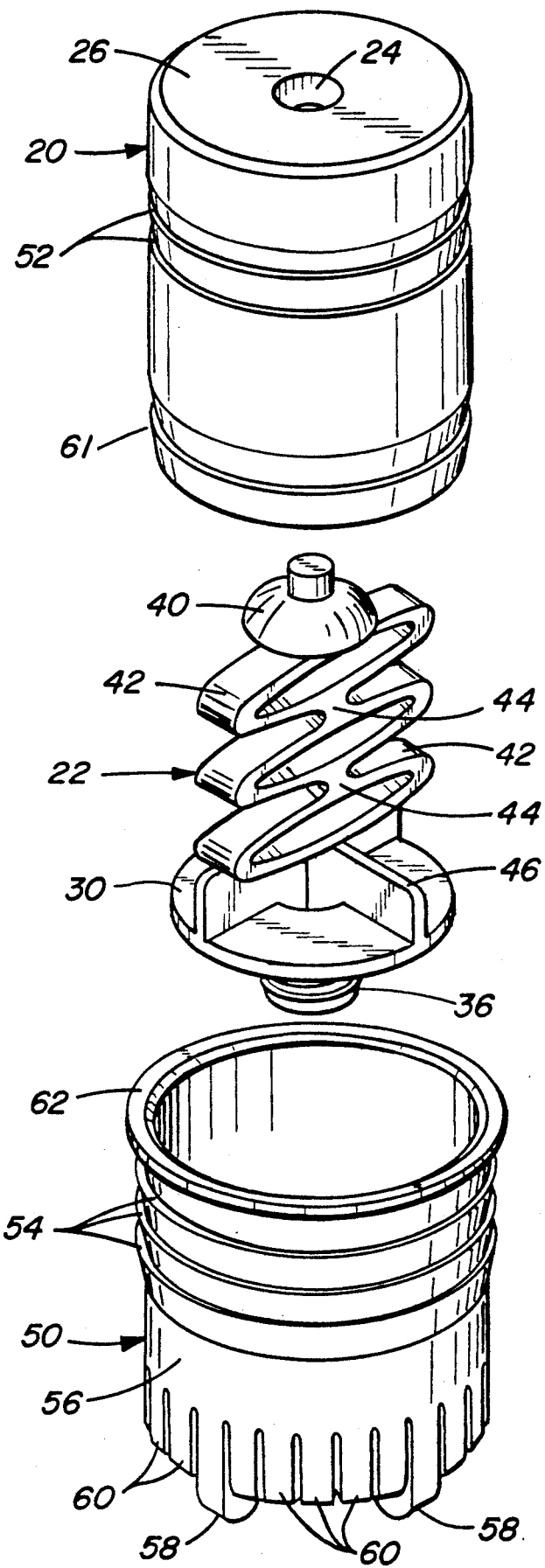
FIG._4.

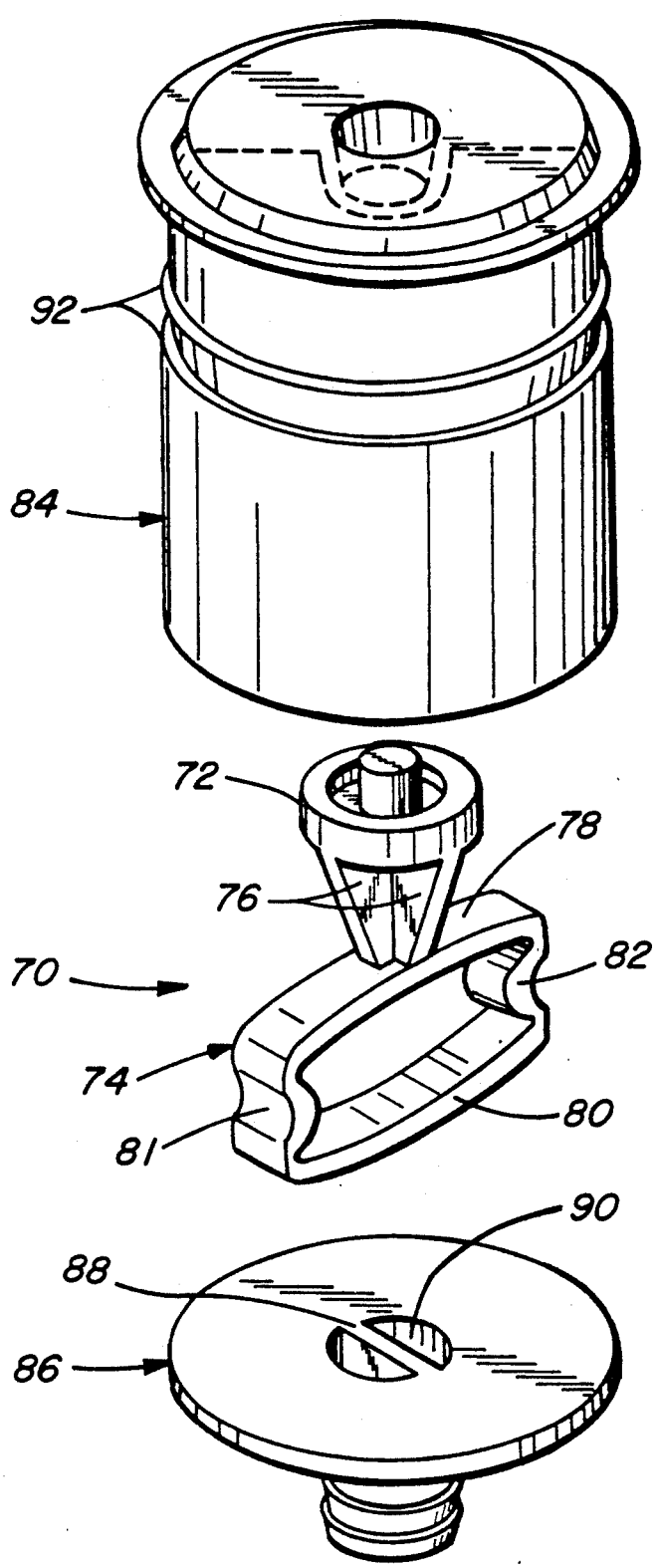
FIG._5.

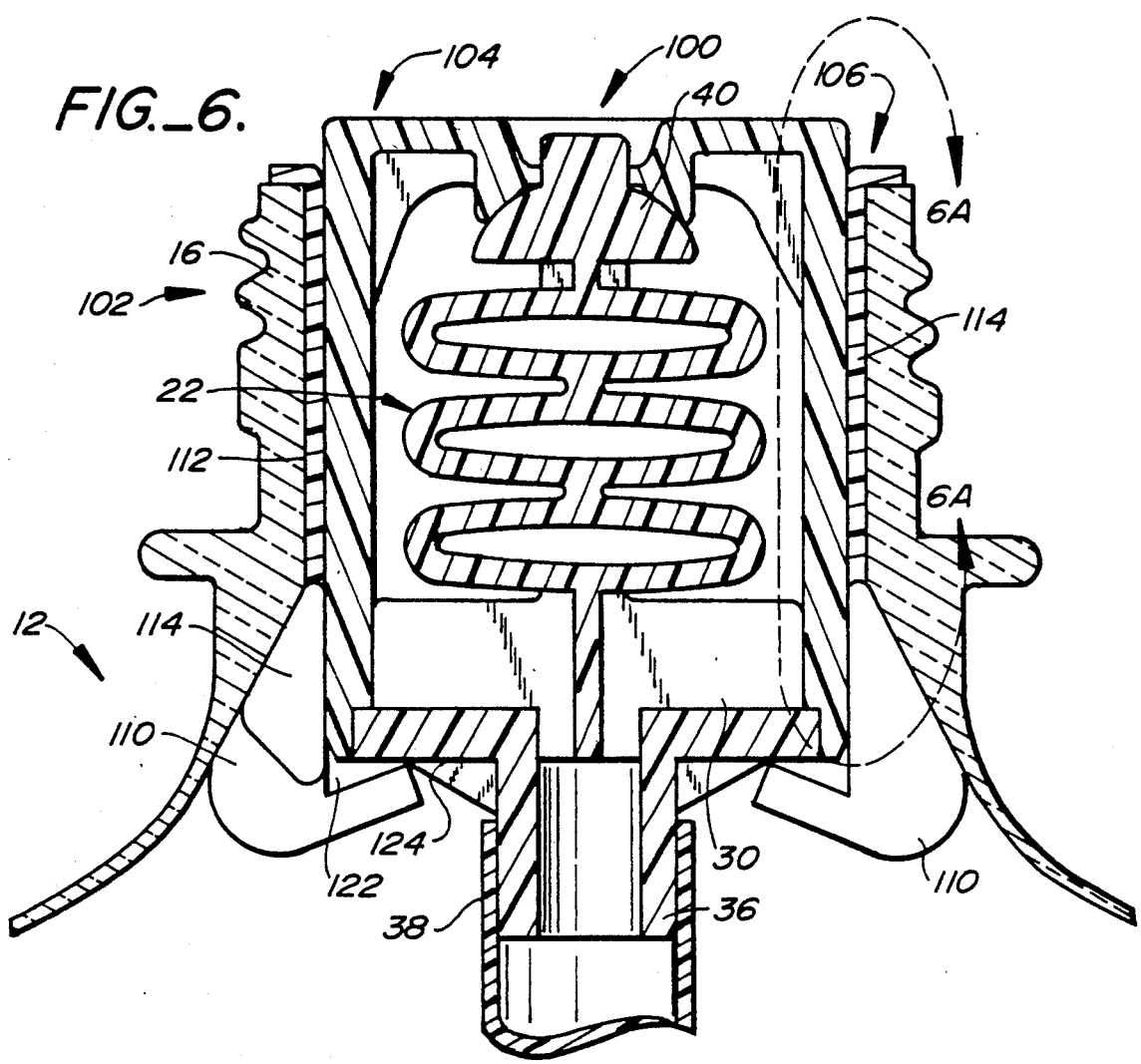
FIG._6.
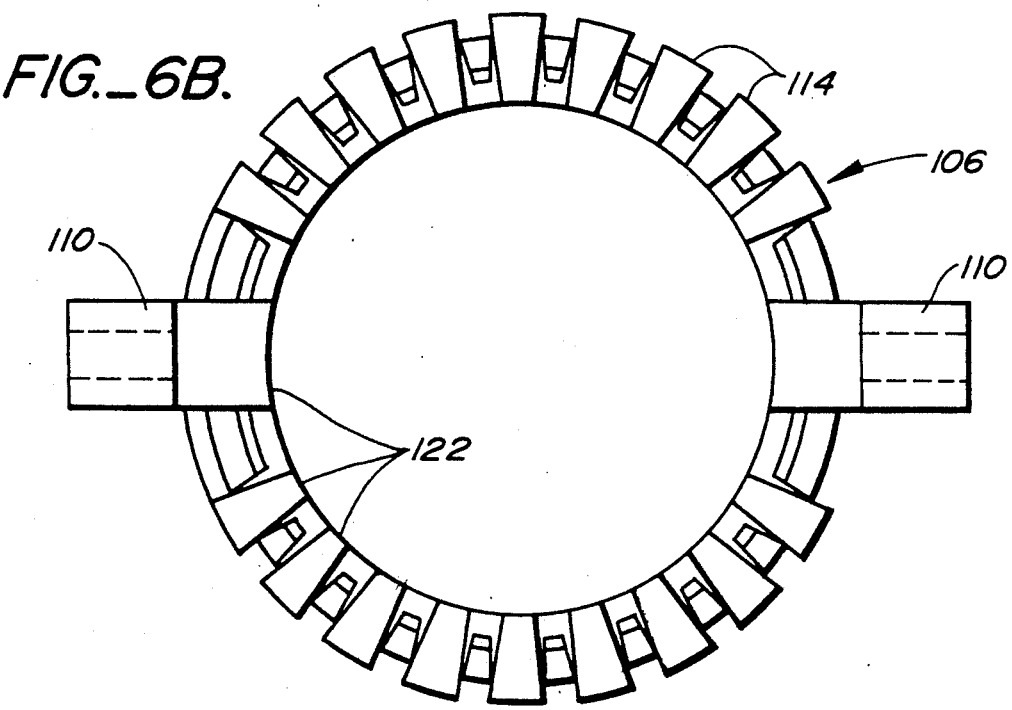
FIG._6B.

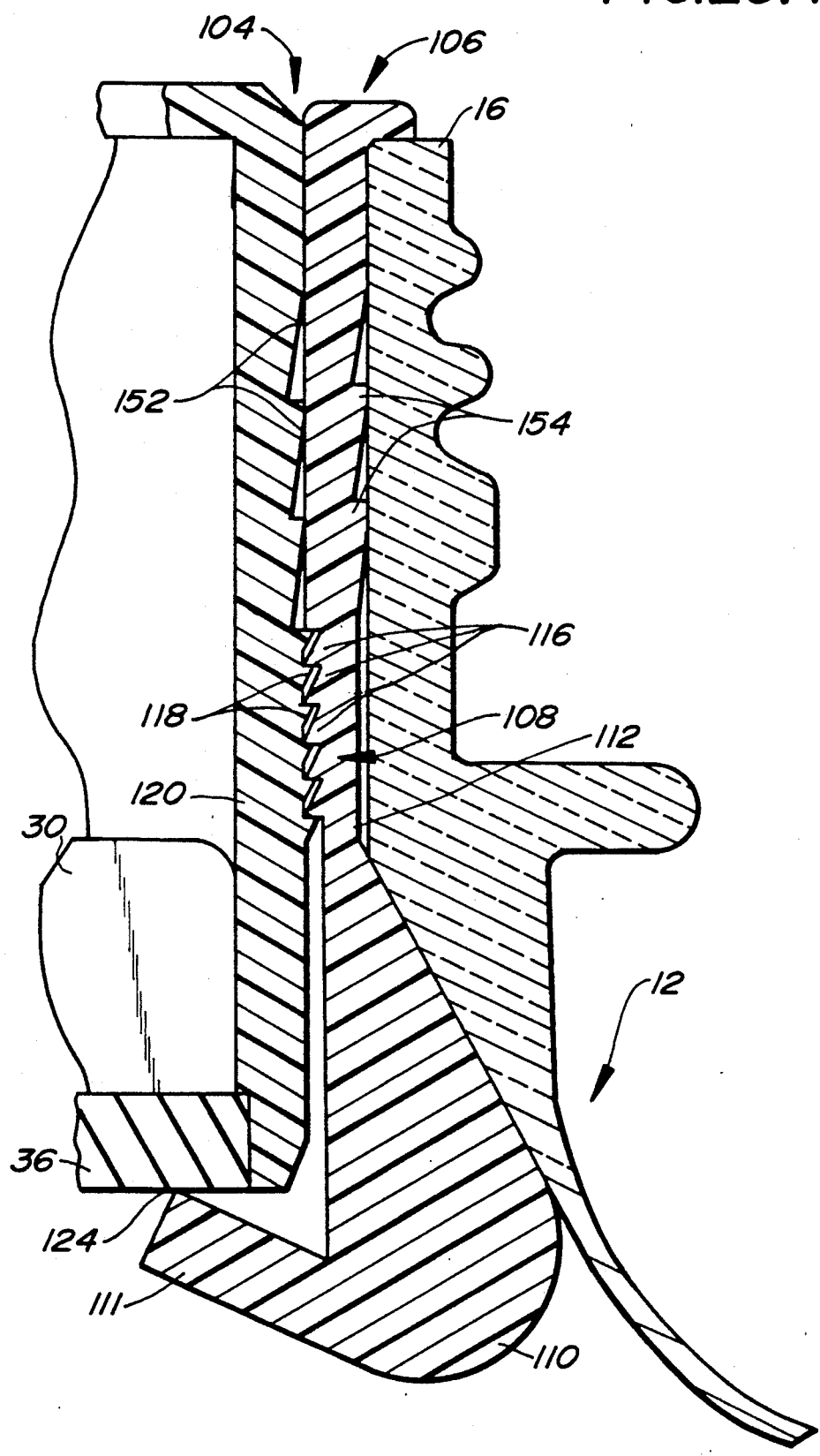
FIG._6A.

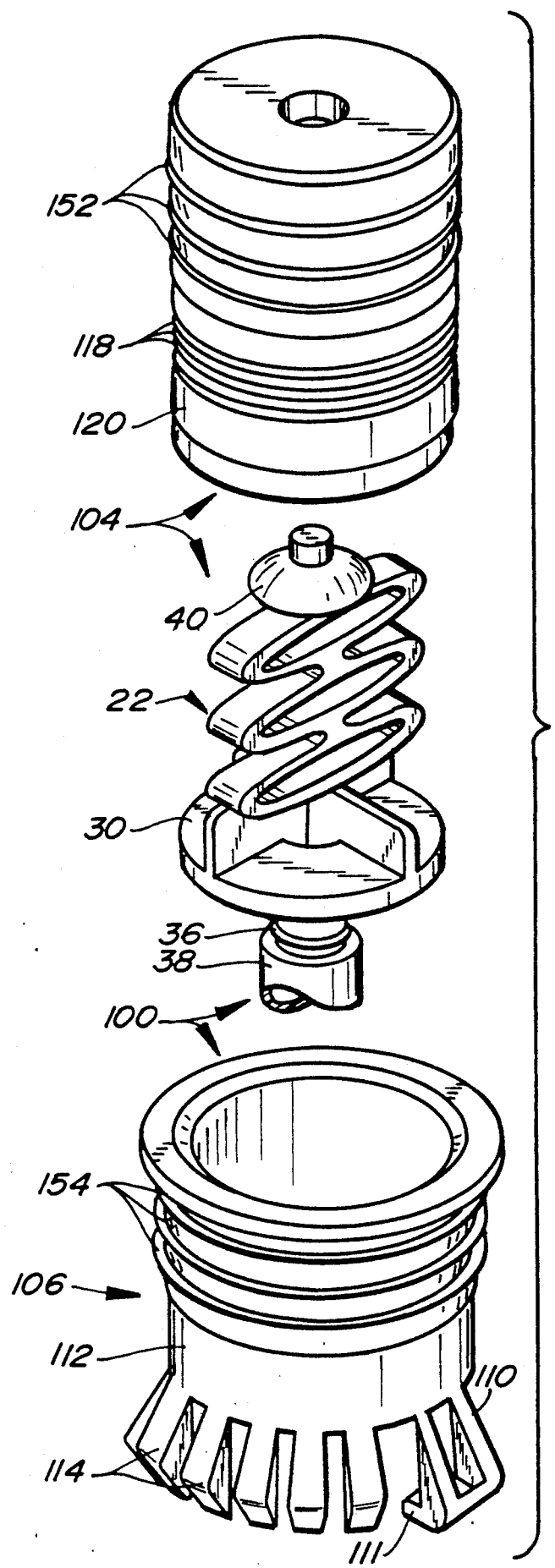
FIG._7.

SYPHON PACKAGE WITH MECHANICALLY ATTACHED VALVE

ORIGIN OF APPLICATION

This application is a continuation-in-part of a copending earlier Application, Ser. No. 07/158,229, filed Feb. 19, 1988, now abandoned, in the names of Richard J. Hagan and Michael D. Clausen, now abandoned.

BACKGROUND OF THE INVENTION

1. Field of the Invention

This invention relates to a novel package for a pressurized fluid. More particularly, it relates to such a package in which a normally closed valve is attached to a necked opening of the package mechanically. Most especially, it relates to such a package in the form of a plastic syphon package for a pressurized liquid, such as seltzer water.

2. Description of the Prior Art

Syphon seltzer water was traditionally supplied in thick walled glass bottles with permanently attached dispensing heads, through which the bottles were filled with carbonated water at a sufficiently high pressure to provide enough force for dispensing all of the water from the bottle. For safety and economic reasons, the traditional syphon seltzer industry has virtually ceased to exist in the United States, although it has continued in certain other countries, most notably Argentina.

More recently, a plastic syphon seltzer bottle has been developed with a removable head. These packages are sold in supermarkets with a conventional twist off cap over a normally closed valve in the necked opening of the bottle. Such plastic syphon seltzer packages are described in the following commonly assigned issued U.S. Patents and pending application: U.S. Pat. No. 4,660,748, issued Apr. 28, 1987 to Hagan; U.S. Pat. No. 4,671,436, issued June 9, 1987 to Hagan; U.S. Pat. No. 4,694,975, issued Sept. 22, 1987 to Hagan; Application Ser. No. 07/008,628, filed Jan. 29, 1987 in the names of Richard J. Hagan and John J. McIntyre, now U.S. Pat. No. 4,773,571.

In these packages, the normally closed valve is contained in a plastic insert that is attached to the inside wall of the necked opening of the bottle by ultrasonic bonding. The ultrasonic attachment process is described in the following commonly assigned pending U.S. applications: Application Ser. No. 06/893,041, filed Aug. 1, 1986 in the name of Richard J. Hagan, now U.S. Pat. No. 4,726,481 and Application Ser. No. 07/030,166, filed Mar. 25, 1987 in the name of Richard J. Hagan now U.S. Pat. No. 4,726,480. In practice, while the ultrasonic bonding process produces very reliable bonding of the valve insert in the necked opening, the ultrasonic bonding process has proved to be a limiting factor in the fabrication rate of the packages. Also, the packages resulting from these ultrasonic packages provide a seal that has proven to be commercially acceptable for the seltzer packages in ordinary supermarket distribution. However, should the packages be heated above about 100 degrees F. for a substantial period of time, relaxation of the plastic in the insert and the necked opening of the bottle can lead to loss of pressurization. This is ordinarily not a problem, even in a hot climate, because it takes a substantial length of time with the package exposed to temperatures above 100 degrees to elevate the package above that temperature because of the volume of water that must be heated to do so. However, it would be desirable to increase the ability of the package to maintain its pressure at elevated temperatures.

The use of ultrasonic bonding to fasten the normally closed valve insert in the necked opening of the bottle means that the bottle cannot be filled with seltzer water until after the insert has been fastened in place. Filling is then accomplished through the normally closed valve and syphon tube by inverting the bottle and opening the valve. An apparatus and process suitable for filling seltzer packages with the valve insert in place is described in U.S. Pat. No. 4,617,973, issued Oct. 21, 1986 to Hagan and Lempert.

In contrast, conventional soft drink bottles are filled with the bottles in an upright position. While the Hagan and Lempert apparatus operates very well to fill the plastic seltzer bottles, the ability to fill the bottles in an upright position would allow the use of slightly modified conventional filling equipment and provide a much higher filling rate than the Hagan and Lempert apparatus.

SUMMARY OF THE INVENTION

Accordingly, it is an object of this invention to provide a design for a normally closed valve insert for a necked opening of a package for a fluid under pressure that does not require ultrasonic bonding for attachment in the necked opening, but which shares the high reliability of the ultrasonic bonding.

It is another object of the invention to provide a package for a fluid under pressure which can be fabricated faster than such a package employing ultrasonic bonding for attaching a normally closed valve insert in a necked opening of the package.

It is a further object of the invention to provide such a package for a fluid under pressure in which the normally closed valve insert is mechanically attached in the necked opening of the package.

It is another object of the invention to provide such a package having an increased ability to maintain its pressure at elevated temperatures over the package employing ultrasonic bonding.

It is still another object of the invention to provide such a package which can be filled in an upright position with slightly modified conventional bottle filling equipment.

It is a still further object of the invention to provide such a package in which parts used to fasten the normally closed valve insert in the necked opening of the package are configured to provide reliable fastening even with dimensional variation in the normally closed valve insert, the parts, and/or the necked opening of the package.

The attainment of these and related objects may be achieved through use of the novel package for a fluid under pressure with a mechanically attached valve insert herein disclosed. A package in accordance with the invention has a container with a necked opening. A normally closed valve insert is in the necked opening of the container. A sleeve is positioned at the necked opening. The necked opening and the sleeve have engaging surfaces configured to hold the sleeve in place at the necked opening. The sleeve is configured to hold the normally closed valve insert in the necked opening against pressure from the pressurized fluid in the container.

The attainment of the foregoing and related objects, advantages and features of the invention should be more readily apparent to those skilled in the art, after review of the following more detailed description of the invention, taken together with the drawings, in which:

BRIEF DESCRIPTION OF THE DRAWINGS

FIG. 1 is an external perspective view of a syphon seltzer package in accordance with the invention.

FIG. 2 is a cross-section view, taken along the line 2—2 in FIG. 1.

FIG. 2A is an enlarged cross-section view of a portion of FIG. 2, to show detail.

FIG. 3 is a cross-section view, taken along the line 3—3 in FIG. 2, but of the entire section at that point.

FIG. 4 is an exploded perspective view of a portion of the syphon seltzer package of FIGS. 1-3.

FIG. 5 is an exploded perspective view of a portion of a second embodiment of a syphon seltzer package in accordance with the invention.

FIG. 6 is a cross-section view of a portion of a third embodiment of a syphon seltzer package in accordance with the invention.

FIG. 6A is an enlarged view of area 6A—6A in FIG. 6.

FIG. 6B is a bottom view of part of the package shown in FIG. 6.

FIG. 7 is an exploded perspective view of part of the syphon seltzer package of FIGS. 6-6B.

DETAILED DESCRIPTION OF THE INVENTION

Turning now to the drawings, more particularly to FIG. 1, there is shown a syphon seltzer package 10 in accordance with the invention. The package 10 consists of a polyethylene terephthalate (PET) plastic bottle 12 capable of withstanding elevated pressures, typically of up to about 10 atmospheres, employed with seltzer water 14 to ensure that there is sufficient pressure remaining in the bottle 12 to discharge the last of the seltzer water 14 from the bottle 12 when it is almost empty. The bottle 12 has a neck 16 with an opening 18, into which a valve insert 20 is mounted. In accordance with this invention, the insert 20 is held in place by mechanical attachment. The valve insert 20 has a poppet 22 (FIG. 2), which is held in sealing engagement at central opening 24 in top 26 of the valve insert 20 until the valve formed by the insert 20 is opened. In practice, the package 10 is filled and a twist off cap (not shown), which is capable of withstanding the pressure inside the package as a safety measure, is attached by external threads 28 on the neck 16 for storage and shipping of the package 10. The consumer removes the twist off cap and replaces it with a dispensing head (not shown) having a lever which is actuable to open the valve formed by the insert 20 to dispense the seltzer water 14 through a spout on the dispensing head. Further details on the construction and operation of the dispensing head are available in the above referenced issued patents and pending applications, the disclosures of which are hereby incorporated by reference herein.

FIGS. 2, 2A, 3 and 4 show details of the insert 20 and the package 10. The insert 20 is generally cylindrical in shape. The poppet 22 fits inside the insert 20 and has a flange 30 which attaches to side 32 of the insert at 34 to form a bottom of the insert 20. The poppet 22, including the flange 30, is formed in a single piece from a molded, resilient plastic material, such as Santoprene, obtainable from Monsanto Chemical Company, St. Louis, Mo. The flange 30 has a fitting 36, to which a syphon tube 38 is attached, extending to the bottom of the bottle 12. A substantially hemispherical shaped head 40 of the poppet 22 is attached to the flange 30 by means of three elliptical shaped leaf springs 42 and connecting links 44. The springs 42 are attached to the flange 30 by a cruciform support 46, which extends across the fitting 36. Similarly, the head 40 is attached to the upper leaf spring 42 by a cruciform support 47. The cruciform supports 46 and 47 provide lateral stability for the poppet 22. An annular lip 48 extends downward from top 26 of the insert 20 around opening 24 to engage the head 40 of the poppet 22. The poppet 22 is dimensioned so that head 40 exerts a positive pressure against the lip 48 when the flange 30 is attached to the wall 32, maintaining the valve formed by the insert 20 and the poppet 22 normally closed.

The insert 20 fits into a sleeve 50 in an interference fit. Projections 52 on the outside of the wall 32 insure a positive seal between the insert 20 and the sleeve 50. Similar projections 54 on the outside surface 56 of the sleeve 50 provide a positive seal between the sleeve 50 and the neck 16 of the bottle 12. At the bottom of the sleeve 50, there are four projections 58 spaced at 90 degree intervals around the sleeve 50. Castellations 60 are provided around the sleeve 50 between the projections 58. Projection 61 at the bottom of the wall 32 fits into detents 63 on the castellations 60 to keep the insert from coming out of the sleeve 50 against the pressure in the bottle 12. The projections 58 retain the flange 30 in place on the bottom of the insert 20 after assembly of the package 10. A lip 62 around the top of the sleeve 50 rests on the neck 16 of the bottle 12.

To assemble the package 10, the sleeve is inserted in the neck 16. The syphon tube is attached to the fitting 36 of the flange 30, and the insert 20 is then driven into the sleeve 50. The interference fit between the insert 20 and the sleeve 50 causes the projections 58 and castellations 60 to splay outward when the insert 20 is fully driven into the sleeve 50. As is best seen in FIG. 2, the outward splaying of the projections 58 and castellations 60 locks the sleeve 50 and insert 20 in place in the neck 16 of the bottle 12. This assembly technique can be carried out at a substantially higher throughput rate than the ultrasonic bonding previously used to attach the insert to the inside of the neck of the bottle.

FIG. 2A shows how the poppet 22 and the annular lip 48 of the insert 20 interact to form a seal at both higher and lower pressures while the package 10 is in use. When the package 10 is filled, a pressurization level of about 100 psi of carbon dioxide is provided in the package 10, in order to provide adequate pressure for discharging the last of the seltzer water 14 from the container as the head space above the water increases. At such higher pressurization levels, the poppet 22 deforms to make contact both at surface 64 and a substantially line contact at 65, as indicated by dotted line 66. The presence of both contacts at the higher pressure levels insures a good seal at those pressures. As the seltzer water 14 is dispensed from the package 10 and the pressure level in the package decreases, the poppet moves out of contact with the surface 64 to the position shown in solid lines, so that only the line contact at 65 is maintained between the poppet and the annular lip 48. The substantially line contact at 65 provides a better seal at lower pressures than the surface contact at 64. The configuration of the poppet 22 and the annular lip 48 and the deformation of the resilient poppet 22 thus provide an effective seal over the entire range of pressures that exist during use of the package 10, from filling to dispensing the last of the seltzer water 14.

FIG. 5 shows another form of a one piece poppet and spring 70 that can be used in the package of the invention. The poppet and spring 70 has a head 72, a single spring 74 and ribs 76 connecting the head 72 and the spring 74. The spring 74 has upper and lower arcuate shaped leaf portions 78 and 80 joined together by inward curved segments 81 and 82. The poppet and spring 70 is used with an insert 84 having similar configuration to that of the insert 20 in FIGS. 2 and 4, but modified to have a separate flange 86 in place of the integral flange 30 of the poppet 22. The flange 86 has a supporting rib 88 for the spring 74 extending across central opening 90 of the flange 86. The insert 84 has a plurality of encircling projections 92 spaced along the substantially vertical wall to insure that the insert 84 and necked opening of the container will maintain their seal at elevated temperatures. The insert 84 can either be fastened in the necked opening with a sleeve in the same manner as the insert 20 or fastened in the necked opening of the bottle with ultrasonic bonding.

Pressure loss tests were carried out with 2 liter plastic bottles having ultrasonically bonded inserts having a single substantially line contact ring seal between the necked opening and the insert with storage at 70° F. and 100° F. The results obtained are shown in Table 1, with the bottles pressurized at 6 and 8 volumes of $CO_2$.

TABLE 1

PRESSURE LOSS
% Loss At Storage Period

| Storage Temperature | CO$_2$ Level | 4 wks | 8 wks | 12 wks | 16 wks | 20 wks | 24 wks |
| --- | --- | --- | --- | --- | --- | --- | --- |
| 70° | 6 vol | .5 | 4.0 | 5.9 | 6.2 | 8.6 | 14.8 |
| 70° | 8 vol | 1.8 | 3.0 | 6.0 | 9.9 | 18.6 | 18.8 |
| 100° | 6 vol | 100.0 | | | | | |
| 100° | 8 vol | 100.0 | | | | | |

These results show that the ultrasonically bonded insert with a single line contact meets bottling industry standards for pressure loss of soda in plastic bottles of no more than 15% pressure loss in 16 weeks when stored at 70° F. However, when the package is stored at 100° F., a rapid loss in pressure occurs, which is believed to be due to relaxation of the plastic of the necked opening and the insert at the more elevated temperature.

Valve inserts having the configuration of the insert 84 in FIG. 5 were subjected to leak tests in order to determine the effectiveness of the encircling projections 92 for reducing pressure loss at 100° F. Bottles filled to a pressure level of 8 volumes of $CO_2$ in which the inserts were held in place with 6 ultrasonic welds in accordance with the teaching of the above referenced related ultrasonic attachment applications were held at 100° F. for one week. Mean pressure loss for the bottles was 32.7%. Minimum pressure loss was 0 and maximum loss was 93.5%, with a standard deviation of 31.32. Previous testing of the inserts having a single line contact between the insert and the neck of the bottle, described above, resulted in a loss of more than 65% of the carbonation for 90% of the bottles during the one week at 100° F. None of the inserts having the encircling projections 92 blew out of the bottles during this test, which was sometimes observed with the prior inserts.

In order to test the retention characteristics of the mechanically attached valve insert as described above, polycarbonate prototype, mechanically attached valve inserts were mounted in the necked opening of plastic seltzer bottles and tested on a pressure testing machine to determine their blow-out pressure at ambient and 100° F., with the results shown in Table 2.

TABLE 2

| Sample Number | Temperature | "Blow-Out" Pressure |
| --- | --- | --- |
| 1 | ambient | 650 psi |
| 2 | ambient | 650 psi |
| 3 | ambient | 680 psi |
| 4 | 100° F. | 600 psi |
| 5 | 100° F. | 600 psi |

For comparison, the ultrasonic welded valve inserts as described in the above-referenced copending applications blow out in the range of 250–450 psi at ambient temperature. The ultrasonic welded valve inserts leak at 200 psi at 100° F. without blowing out.

FIGS. 6–7 show a third form of a valve insert assembly 100 that is used to form a syphon seltzer package 102. The valve insert assembly 100 uses the same integral poppet 22 and syphon tube flange 30 as in the FIGS. 1–4 embodiment, and the normally closed valve formed by the poppet 22 and insert 104 therefore functions in the same manner as in the FIGS. 1–4 form of the invention.

The valve insert assembly 100 includes the valve insert 104 and a sleeve 106 that incorporate a fastening mechanism 108 (FIG. 6A) that will hold the valve insert assembly securely and reliably in place in the neck 16 of the PET bottle 12, regardless of variations in the dimensions of the neck 16. It should be noted that the PET bottle 12 is fabricated by a blow molding process. The nature of such a process produces considerable dimensional variation in the configuration of the bottle 12, including the neck 16.

The fastening mechanism 108 is constructed as follows: Sleeve 106 has a pair of projections 110 spaced at a 180 degree interval around the sleeve 106 at the bottom of wall 112. There are two of the projections 110 at each location, joined together at their bottom by portions 111. Castellations 114 are provided around the sleeve 106 between the projections 110. Sleeve 106 has a series of ratchet ribs 116 extending around the wall 112 on its inside surface. Valve insert 104 has a mating series of ratchet ribs 118 around wall 120 on its outside surface. The valve insert 104 is dimensioned for interference fit in the sleeve 106, and the sleeve 106 is dimensioned for interference fit in the neck 16 of the bottle 12, in the same manner as the valve insert 20 and the sleeve 50 of the FIGS. 1–4 embodiment.

The valve insert assembly 100 is inserted in the neck 16 of the bottle 12 to form the package 102 in the following manner. The bottle 12 is first filled with seltzer by a conventional straight up filling operation as employed for filling bottles with carbonated beverages. The sleeve 106 is then placed in the neck 16. The projections 110 and the castellations 114 deflect inward in order to allow the sleeve 106 to fit into the neck 16. The valve insert 104, with syphon tube 38 in place, is then driven into the sleeve 106 until the ratchet ribs 116 and 118 interlock to attach the sleeve and valve insert 104 together in the neck 16. The sleeve 106 and the valve insert 104 are now held securely in the neck 16 against the pressure of the seltzer by the projections 110 and the castellations 114, because the projections 110 and the castellations are prevented from deflecting inward by the valve insert 104.

In order for the ratchet ribs 116 and 118 to lock the valve insert 104 and the sleeve 106 together, there can be as few as one or two of the ribs 116 and 118 in overlying relationship at either end, or the series of ribs 116 and 118 can be completely in overlying relationship. This extent of variation in the relative positioning for function of the ribs 116 and 118 means that the valve insert assembly 100 can be used with the entire range of dimensional variations of the necked opening 16 that is likely to be encountered in practice.

Portions 111 of the projections 110 engage the syphon tube flange 30 at 124 to help keep the syphon tube flange 30 in place at the bottom of the insert 104. The syphon tube flange 30 fits against wall 120 of the insert 104 in an interference fit, and the portions 111 prevent separation of the flange 30 from the wall 120, particularly at lower pressures in the bottle 12, when it is nearly empty, and force of the spring of the poppet 22 might otherwise cause such separation to take place.

As in the FIGS. 1-4 embodiment, projections 152 on the outside wall 120 of the insert 104 provide a positive seal between the insert 104 and the sleeve 106. Similarly, projections 154 on the outside of sleeve 106 provide a positive seal between the sleeve 106 and the neck 16 of the bottle 12. Other than as shown and described, the construction and operation of the FIGS. 6-7 embodiment of the invention is the same as that of the FIGS. 1-4 embodiment.

It should now be readily apparent to those skilled in the art that a novel package for a pressurized fluid capable of achieving the stated objects of the invention has been provided. The package of this invention provides a mechanical attachment for a normally closed valve insert in the necked opening of the container. The mechanical attachment can be provided much more rapidly than the ultrasonic bond it replaces, but shares the high reliability of the ultrasonic bonding. The mechanical attachment assembly can be provided in form that will accommodate any dimensional variation likely to be encountered in the containers of the package.

It should further be apparent to those skilled in the art that various changes in form and details of the invention as shown and described may be made. It is intended that such changes be included within the spirit and scope of the claims appended hereto.

What is claimed is:

1. A package for a pressurized fluid, which comprises a container having a necked opening, a normally closed valve insert in the necked opening of said container, said container having a portion of increased width immediately below the necked opening, and a plurality of attaching members extending between said normally closed valve insert and the portion of increased width and mechanically holding said normally closed valve insert within the necked opening, said plurality of attaching members being provided on a sleeve positioned in the necked opening between said normally closed valve insert and the necked opening, said normally closed valve insert being dimensioned for an interference fit in said sleeve, said plurality of attaching members being held in a splayed position by said normally closed valve insert to hold said normally closed valve insert and said sleeve within the necked opening, said plurality of attaching members comprising spaced apart projections extending downward from said sleeve a first distance and a plurality of castellations between each of the spaced apart projections, said plurality of castellations extending downward from said sleeve a second distance less than the first distance.

2. The package for a pressurized fluid of claim 1 in which said plurality of spaced apart projections are positioned at 180 degree intervals around said sleeve relative to one another.

3. The package for a pressurized fluid of claim 2 in which there are a pair of said projections at each 180 degree interval around said sleeve.

4. The package for a pressurized fluid of claim 3 in which each pair of said projections is joined together by a bottom portion.

5. The package for a pressurized fluid of claim 1 in which said sleeve and said valve insert have facing substantially vertical surfaces, and there are a plurality of ring projections extending completely around said sleeve and said valve insert, making a plurality of substantially line contacts between the facing surfaces and being longitudinally spaced along said valve insert and said sleeve.

6. The package for a pressurized fluid of claim 5 in which said plurality of ring projections are on said valve insert.

7. The package for a pressurized fluid of claim 6 in which said sleeve and the necked opening have facing substantially vertical surfaces, and there are a second plurality of ring projections extending completely around said sleeve and the necked opening, making a plurality of substantially line contacts between the facing surfaces and being longitudinally spaced along said sleeve and the necked opening.

8. The package for a pressurized fluid of claim 7 in which said second plurality of ring projections are on said sleeve.

9. The package for a pressurized fluid of claim 8 in which the pressurized fluid is a liquid and said package includes a syphon tube attached to the flange and extending down in the container proximate to a bottom of the container.

10. The package for a pressurized fluid of claim 1 in which said normally closed valve includes a poppet formed in a single piece from plastic and including a head, a flange forming a bottom of said normally closed valve insert and at least one spring connected between the head and the flange.

11. The package for a pressurized fluid of claim 10 in which said projections have a bottom portion which extends inward to engage an underside of the flange.

12. The package for a pressurized fluid of claim 11 in which there are a pair of said projections at each 180 degree interval around said sleeve and the pair of said projections are joined by the bottom portion.

13. The package for a pressurized liquid of claim 11 in which said at least one spring comprises a plurality of interconnected substantially elliptical leaf springs.

14. The package for a pressurized liquid of claim 10 in which said poppet and said valve insert are configured to form at least a surface seal between mating surfaces of said poppet and said valve insert at higher pressures in said package and a substantially line contact seal between said poppet and said mating surfaces at lower pressures in said package.

15. A package for a pressurized fluid, which comprises a container having a necked opening, a normally closed valve insert in the necked opening of said container, said container having a portion of increased width immediately below the necked opening, and a plurality of attaching members extending between said normally closed valve insert and the portion of increased width and mechanically holding said normally closed valve insert within the necked opening, said normally closed valve including a poppet formed in a single piece from plastic and including a head, a flange forming a bottom of said normally closed valve insert and at least one spring connected between the head and the flange, the pressurized fluid is a liquid and said package including a syphon tube attached to the flange and extending down in the container proximate to a bottom of the container, said at least one spring comprising a plurality of interconnected substantially elliptical leaf springs, the flange having a central opening defining a fitting for attaching said syphon tube to the flange and said interconnected plurality of leaf springs being attached to said flange by means of a cruciform support extending across the central opening.

16. A package for a pressurized fluid, which comprises a container having a necked opening, a normally closed valve insert in the necked opening of said container, said container having a portion of increased width immediately below the necked opening, and a plurality of attaching members extending between said normally closed valve insert and the portion of increased width and mechanically holding said normally closed valve insert within the necked opening, said normally closed valve including a poppet formed in a single piece from plastic and including a head, a flange forming a bottom of said normally closed valve insert and at least one spring connected between the head and the flange, said poppet and said valve insert being configured to form at least a surface seal between mating surfaces of said poppet and said valve insert at higher pressures in said package and a substantially line contact seal between said poppet and said mating surfaces at lower pressures in said package, said poppet having a head with a substantially hemispherical mating surface against the mating surface of said valve insert at the higher pressures, the mating surface of said valve insert having an annular projection forming the substantially line contact seal with the substantially hemispherical mating surface at the lower pressures.

17. A package for a pressurized fluid, which comprises a container having a necked opening, a normally closed valve insert in the necked opening of said container, a sleeve positioned at said necked opening, said necked opening and said sleeve having engaging surfaces configured to hold said sleeve in place at said necked opening, and said sleeve being configured to hold said normally closed valve insert in the necked opening against pressure from the pressurized fluid in said container, said sleeve being between said valve insert and said necked opening, said container having a portion of increased width immediately below the necked opening and said sleeve being configured to hold said normally closed valve insert in the necked opening by having a plurality of projections around a lower edge which are held in a splayed position by said normally closed valve insert into the portion of increased width of said container, said plurality of projections comprising first spaced apart projections extending downward from said sleeve a first distance and a plurality of castellations between each of the first spaced apart projections, said plurality of castellations extending downward from said sleeve a second distance less than the first distance.

18. The package for a pressurized fluid of claim 17 in which said plurality of spaced apart projections are positioned at 180 degree intervals around said sleeve relative to one another.

19. The package for a pressurized fluid of claim 18 in which there are a pair of said projections at each 180 degree interval around said sleeve.

20. A package for a pressurized fluid, which comprises a container having a necked opening, a normally closed valve insert in the necked opening of said container, a sleeve positioned at said necked opening, said necked opening and said sleeve having engaging surfaces configured to hold said sleeve in place at said necked opening, and said sleeve being configured to hold said normally closed valve insert in the necked opening against pressure from the pressurized fluid in said container, said normally closed valve including a poppet formed in a single piece from plastic and including a head, a flange forming a bottom of said normally closed valve insert and at least one spring connected between the head and said flange, the pressurized fluid being a liquid and said package including a syphon tube attached to said flange and extending down in the container proximate to a bottom of the container, said at least one spring comprising a plurality of interconnected substantially elliptical leaf springs, said poppet and said valve insert being configured to form at least a surface seal between mating surfaces of said poppet and said valve insert at higher pressures in said package and a substantially line contact seal between said poppet and said mating surfaces at lower pressures in said package, said flange having a central opening defining a fitting for attaching said syphon tube to said flange and said interconnected plurality of leaf springs being attached to said flange by means of a cruciform support extending across the central opening.

21. A package for a pressurized fluid, which comprises a container having a necked opening, a normally closed valve insert in the necked opening of said container, a sleeve positioned at said necked opening, said necked opening and said sleeve having engaging surfaces configured to hold said sleeve in place at said necked opening, and said sleeve being configured to hold said normally closed valve insert in the necked opening against pressure from the pressurized fluid in said container, said normally closed valve including a poppet formed in a single piece from plastic and including a head, a flange forming a bottom of said normally closed valve insert and at least one spring connected between the head and the flange, said poppet and said valve insert being configured to form at least a surface seal between mating surfaces of said poppet and said valve insert at higher pressures in said package and a substantially line contact seal between said poppet and said mating surfaces at lower pressures in said package, the head of said poppet having a substantially hemispherical mating surface against the mating surface of said valve insert at the higher pressures, the mating surface of said valve insert having an annular projection forming the substantially line contact seal with the substantially hemispherical mating surface at the lower pressures.

22. A package for a pressurized fluid, which comprises a container having a necked opening, a normally closed valve insert in the necked opening of said container, and a one piece, integrally formed poppet in said normally closed valve insert, said one piece, integrally formed poppet and said valve insert being configured to form at least a surface seal between mating surfaces of said one piece, integrally formed poppet and said valve insert at higher pressures in said package and a substantially line contact seal between said one piece, integrally formed poppet and the valve insert at lower pressures in said package.

23. The package for a pressurized fluid of claim 22 in which said poppet has a head with a substantially hemispherical mating surface against the mating surface of said valve insert at the higher pressures, the mating surface of said valve insert having an annular projection engaging the substantially hemispherical mating surface to form the substantially line contact seal at the lower pressures.

* * * * *